United States Patent [19]

Miller

[11] Patent Number: 5,384,103

[45] Date of Patent: Jan. 24, 1995

[54] INSTRUMENT TRAY

[75] Inventor: Curtis H. Miller, Burnsville, Minn.

[73] Assignee: Micromedics, Inc., Eagan, Minn.

[21] Appl. No.: 149,030

[22] Filed: Nov. 8, 1993

Related U.S. Application Data

[63] Continuation of Ser. No. 853,034, Mar. 17, 1992, abandoned.

[51] Int. Cl.⁶ .................................................. A61L 2/06
[52] U.S. Cl. .................................... 422/310; 422/300;
422/297; 16/115; 16/112; 403/348; 211/60.1;
211/194; 220/315; 206/509; 206/511; 206/508
[58] Field of Search ............... 422/297, 300; 211/60.1,
211/94, 126, 162, 188, 194; 220/315; 292/202,
213, 208, 304; 206/508, 509, 511; 403/348;
16/115, 112

[56] References Cited

U.S. PATENT DOCUMENTS

| | | | |
|---|---|---|---|
| 2,645,332 | 7/1953 | Martin et al. | 220/315 |
| 2,659,642 | 11/1953 | Records | 211/94 |
| 2,898,122 | 8/1959 | Beckner | 206/511 |
| 3,030,163 | 4/1962 | Gottsegen | 206/509 |
| 3,493,722 | 2/1970 | Popeil | 422/300 |
| 3,788,689 | 1/1974 | Lloyd | 292/304 |
| 3,812,279 | 5/1974 | Voegeli | 292/304 |
| 3,980,185 | 9/1976 | Cain | 206/509 |
| 4,135,868 | 1/1979 | Schainholz | 422/300 |
| 4,175,781 | 11/1979 | Dumortier | 292/218 |
| 4,541,992 | 9/1985 | Jerge et al. | 422/300 |
| 4,562,047 | 12/1985 | Sestak et al. | 422/300 |
| 4,617,178 | 10/1986 | Nichols | 422/300 |
| 4,643,303 | 2/1987 | Arp et al. | 422/300 |
| 4,730,729 | 3/1988 | Monch | 422/300 |
| 4,762,688 | 8/1988 | Berry, Jr. | 422/300 |
| 4,783,321 | 11/1988 | Spence | 422/300 |
| 4,798,292 | 1/1989 | Hauze | 422/300 |
| 4,915,913 | 4/1990 | Williams et al. | 422/300 |
| 4,928,917 | 5/1990 | Wolf | 422/300 |
| 4,959,199 | 9/1990 | Brewer | 422/300 |
| 5,155,960 | 10/1992 | Shaanan | 403/348 |
| 5,215,726 | 6/1993 | Kudla et al. | 422/297 |

*Primary Examiner*—Robert J. Warden
*Assistant Examiner*—Hien Tran
*Attorney, Agent, or Firm*—Kinney & Lange

[57] ABSTRACT

An instrument tray assembly including a tray and an optional cover for the storage, transport and sterilization of medical instruments is disclosed. Each tray and cover is perforated to permit the flow of sterilizing medium therethrough, and each is comprised of materials which will withstand soaking and steam or gas autoclaving. Interchangeably disposed along the surfaces of the tray and cover are a plurality of support members, each including variously dimensioned notched receptacles for receiving medical instruments. Each tray may also include a set of handles which may be extended at a variety of angles, thereby avoiding contact and possible contamination between gloved hands and instruments, depending upon the orientation of each handle. Alternative embodiments for resilient instrument support members are disclosed. One embodiment includes resilient projections which are insertable directly into the perforations on the trays and covers. An alternative embodiment further includes a rigid extrusion. The extrusion is screwed to the surface of the tray or cover and the instruments are inserted into variously dimensioned receptacles on the support mounts. The trays may be used independently, interlockingly stacked one upon another, used in association with a locking cover, or covered then stacked together. The unique structure of the feet permits the trays to interlock in any of these combinations, to prohibit damage to the instruments contained therein. Optional locks which engage the cover further secure the instruments.

15 Claims, 3 Drawing Sheets

INSTRUMENT TRAY

This is a continuation of application Ser. No. 07/853,034, filed Mar. 17, 1992, now abandoned.

BACKGROUND OF THE INVENTION

I. Field of the Invention

This invention relates generally to the design of trays for sterilization and storage of surgical instruments and more particularly to a stackable instrument tray having a perforated base and cover and including cushions which securely receive and grip a plurality of instruments in place to prevent damage to the instruments during handling in a hospital or clinic environment.

II. Discussion of the Prior Art

A variety of containers have been devised for the sterilization and storage of medical instruments. Typically, they include a storage basket or insert which is dimensioned to fit loosely within a rigid box-like structure. These containers are available with or without a cover and some include ribs or retaining posts which pinch against various instruments and hold them in place. Although care is taken in the loading, sterilization, and storage of instruments within these containers, occasionally one is dropped or otherwise subjected to force which dislodges the instruments. Should this occurs, the delicate instruments stored within can be damaged.

An example of an autoclave tray for surgical apparatus is disclosed in U.S. Pat. No. 4,762,688, issued to Berry, Jr. This essentially flat tray is dimensioned to permit placement within a basket-like structure, or to be individually wrapped in surgical drapes. The surface of the tray includes both a plurality of steam holes disposed in a predetermined pattern along the surface, and a plurality of keyholes which receive extensions from synthetic plastic instrument holders which provide braces for various instruments. Each holder includes a base portion, a body portion, and a connecting portion, wherein the connecting portion is narrower than either the base or body portions and the body portion is slotted to receive and hold a portion of a surgical instrument. It has been our experience that when severely jarred, the instruments stored in the Berry style tray may become dislodged from its slot in the body portion of this holder. Moreover, no provision is made to allow several such trays to be conveniently stacked in an autoclave or in a storage cabinet.

Modular supports for protecting instruments within a sterilization tray are disclosed in U.S. Pat. No. 4,135,868, issued to Schainholz. The supports are provided in pairs, one being inserted into the cover of the sterilization tray and the other being complimentarily inserted into a molded, rectangular instrument support base to which the cover is hinged. Both the cover and the support base include perforated surfaces into which extensions from the modular supports may be inserted. Thus, the modular supports may be placed at a variety of angles and positions within the tray. The modular supports include variously shaped cutouts, dimensioned to receive a variety of instruments. However, the cutouts are not specifically tailored for individual instruments, so direct pressure from the modular supports mounted in the cover is relied upon to maintain proper positioning of the instruments. If this instrument tray is inadvertently dropped, it is possible for the securing latch between the base and cover to pop open, causing the clamping pressure on the instruments to be released and permitting them to become dislodged and damaged. Again, no provision is made for the stable stacking of a plurality of such trays, one upon the other.

It is accordingly a principal object of the present invention to provide an instrument tray for the sterilization and storage of surgical instruments which includes instrument holders that securely grasp individual instruments and do not permit them to become dislodged during severe jarring of the tray.

It is a further object of the present invention to provide instrument trays which may be interlockingly stacked for secure storage of multiple trays.

It is yet another object of this invention to provide a new and improved instrument tray assembly having a securely locking cover which will not dislodge if the tray is dropped or jarred.

A further object of the present invention is to provide a new and improved instrument tray having a unique set of retracting handles which may be grasped and held at a variety of angles, thereby permitting sterilized trays to be easily transferred without contamination.

A still further object of the present invention is to provide a new and improved apparatus for an instrument tray having a unique, locking mechanism that will assure the instrument tray cover remains properly in place as the tray is tilted at all angles.

SUMMARY OF THE INVENTION

The foregoing objects and advantages of the invention are achieved by providing a tray for sterilizing surgical instruments, made of anodized aluminum or other heat-resistant, rigid material, enabling it to be used for either steam or gas autoclaving, or for sterilization by soaking. It features a floor having a pattern of perforations therethrough and a detachable cover also with perforations. A variety of flexible, instrument retaining support members are designed to either affix to or fit into selected ones of the perforations within the base and cover of the tray, to receive various instruments and prevent them from sliding. The remaining perforations allow for the ready ingress of a sterilant, e.g., steam, ethylene oxide or a liquid, such as Cidex. The support members or mounts further include receptacles that are specially contoured to appropriately encompass portions of medical instruments, to resiliently grip them more securely than the instrument supports available in prior art equipment. The feet of the tray are contoured to either securely engage the mutually perpendicular sides of a tray placed beneath them at their corners, or to be stabilized by partially extending through special openings formed in a cover of the lower tray assembly. Thus, the unique feet permit trays to be interlocked when they are stacked, whether or not covers are used.

A handle is comprised of a rigid, generally U-shaped steel rod that fits within a pair of clips or brackets affixed to the inner surface of the side of the tray. The unique design of the handle and associated brackets permits it to be positioned to extend through the cover, to be retracted against the side of the tray where it does not interfere with the stacking of plural trays, to be horizontally aligned above the surface or the tray for ease of gripping, or to be oriented at any angle therebetween. The trays of the present invention are dimensioned to fit within commercially available sterilizing capsules or containers widely used in a hospital's Central Sterilization Department. Because the handles may be extended at a variety of angles, it enables a nurse or technician wearing sterile gloves to readily grasp the handles at an angle and, thus, they may more easily avoid contacting any non-sterile surfaces on the capsule, as the tray is removed from within. Placing the handles at an appropriate angle may also avoid contact with any other surfaces that may contaminate his or her gloves.

The optional cover having a planar top and four depending side walls is dimensioned slightly larger than the base of the tray. A pair of rigid, plastic locks are positioned at opposing ends of the tray, to positively engage the cover and hold it in place relative to the base. When a grasping pin extending from the lock is rotated into a position where it rests horizontally, the cover is locked to the tray by the mechanical obstruction of a slot in the cover, but when the pin is placed vertically, the lock has been rotated to present a narrower profile, allowing it to pass through a slot in the sidewall of a cover as the cover is lifted from the tray base. The cover cannot come off even if the tray is dropped because of the unique lock arrangement employed.

The advantages of the present invention over the prior art include a greater flexibility in supporting a wide variety of variously dimensioned instruments. The many shapes available for the receptacles within the support members, which are specially tailored to receive various medical instruments of differing shape configuration, and the support members themselves being interchangeable and positionable anywhere along the perforated surfaces of the tray's floor and cover allows for the secure retention of the contained instruments, even if the tray is inverted. Also, the lock arrangement employed precludes the cover from coming off unless the lock is released. Thus, delicate instruments are more securely protected within the support members if the tray is inadvertently dropped.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE PREFERRED EMBODIMENT

Figure 1:
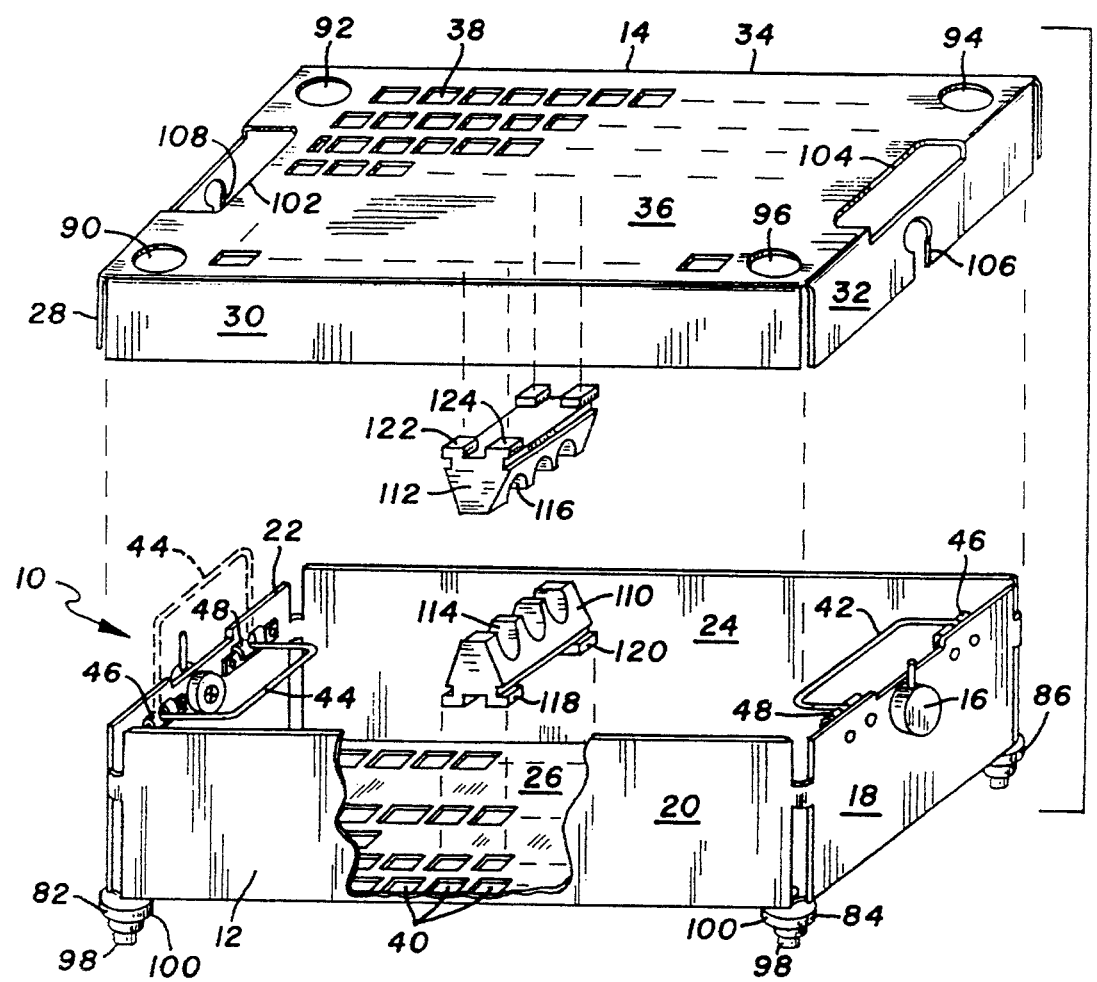
FIG. 1 is an exploded perspective view of a preferred embodiment of the instrument tray and detachable cover.

FIG. 1 is a perspective view of the instrument tray and cover assembly of the present invention, generally designated 10. It includes a base or tray 12 and cover 14, which are adapted to be secured together using a lock 16. The tray includes mutually perpendicular walls 18, 20, 22 and 24, with bottom panel or floor 26. The walls are more particularly end walls 18 and 22, and side walls 20 and 24. The cover 14 includes downwardly depending walls 28, 30, 32 and 34, with top panel 36. Both bottom panel 26 and top panel 36 include a pattern of rectangular perforations, as at 38 and 40, to permit steam or other sterilizing medium to freely pass through the instrument tray assembly 10 and thereby access all instruments held therein. The tray 12 and cover 14 are preferably formed from flat sheets of anodized aluminum which are first subjected to a metal stamping operating to crate the pattern of apertures and then are bent in a break to create the mutually perpendicular walls. It is to be noted that the adjacent walls of the cover and tray do not meet, but instead are spaced apart by a slight gap. This facilitates cleaning.

Affixed to the end walls 18 and 22 of the tray 12 are a pair of handles 42 and 44, each mounted in brackets, as at 46 and 48. Each handle 42 and 44 is comprised of a cylindrical steel or aluminum rod, bent appropriately into a general U-shape to receive the width of a hand. The terminal ends of the handles are bent orthogonal to its legs.

Figure 2:
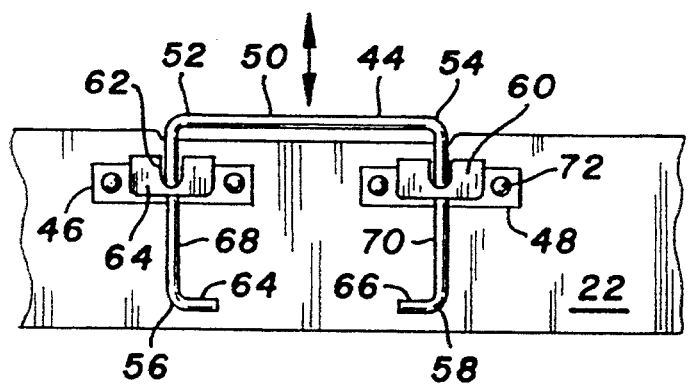
FIG. 2 is a plan view of a portion of the end wall of the tray base showing the retractable handle of the instrument tray of FIG. 1.

The components of handles 42 and 44 are shown in greater detail in FIG. 2. Although described in reference to handle 44, handle 42 is similarly constructed. The portion of handle 44 which is dimensioned to receive the user's fingers is identified as 50 and is comprised of a cylindrical rod which is bent at right angles at corners 52, 54, 56 and 58. The corners 52 and 54 advantageously permit the handle to slide within slots 60 and 62 formed in brackets 46 and 48. Slots 60 and 62 are formed by creating an elongated slot in a flat blank, then bending the blank at the site of the hole such that a channel is created having a width slightly larger than the diameter of the cylindrical rod 44 comprising handle. The feet 64 and 66 on the terminal ends of legs 68 and 70 prevent handle 44 from being pulled completely through the slots 60 and 62 in brackets 46 and 48. Brackets 46 and 48 are riveted, screwed or otherwise secured, as at 72, to sides 18 and 22 of the instrument tray 12.

In use, the handles 42 and 44 may be drawn upwards until the feet 64 and 66 reside in the bracket's channels adjacent to the slots 60 and 62. Because these slots extend vertically along the surface 64 to a depth which is equal to the diameter of the cylindrical handle 42, the handles will lie parallel to the floor surface of the tray when extended towards one another. Typically, however, the handles are retracted along the side of the tray as the instrument tray is sterilized. During sterilization, the tray is typically either wrapped in cloth drapes, and unwrapped just prior to use, or placed within a rigid capsule or container. After the capsule is opened to expose the tray, each handle may be accessed by grasping it with a single finger. Lifting each handle permits it to be oriented at a variety of angles with respect to the sides of the tray, so that the tray may be lifted without the fingers touching either the sides of the capsule or the instruments therein. The handle 44, when in the position shown in phantom line in FIG. 1, indicates the maximum excursion or swing from the bottom panel that is permitted by this handle configuration.

Affixed to the undersurface of the tray's floor 26 proximate the four corners thereof are foot members, only foot members 82, 84 and 86 being visible in the view of FIG. 1. The four foot members are specially dimensioned to be insertable either into circular apertures 90, 92, 94 and 96 formed through the cover 14 at its corners, or stackable with a juxtaposed uncovered tray 12. Because the trays may be used with or without a cover, each foot members includes at least two cylindrical, stepped regions, as at 98 and 100 which a shoulder is defined between each pair of stepped regions. The smaller of the stepped regions (98) are insertable into the circular holes 90, 92, 94, 96 formed in the cover, while the larger stepped regions (100) abut the upper edges of the tray's walls 18, 20, 22 and 24 and engage them when one tray is set on top of another tray.

As indicated at foot member 82, a circular disk portion is formed coextensively with the cylindrical foot members and lies along the underside of the bottom panel 26. The larger stepped region 100 is dimensioned to project beyond the corner formed at the intersection of, for example, walls 20 and 22 of an underlying tray. Each foot members includes a similar retaining disk. Thus, the unique shape of the foot members permits the trays 12 to be stacked upon one another without requiring cover 14 and when uncovered trays are stacked, they are mechanically obstructed from laterally shifting and collapsing into the tray below. Each of the foot members is secured to the underside of bottom panel 26 using a screw (not shown), which passes through a hole drilled at each corner of the tray and into the feet.

Turning now to cover 14, the top panel 36 is slightly larger in surface area than bottom panel 26 of the tray 12. It includes the circular corner openings 90, 92, 94, and 96 which are dimensioned to receive the small stepped regions 98 of the foot members. When the feet of one tray are inserted within the openings 90, 92, 94, 96 of the cover on an underlying tray, they cannot become dislodged from one another, even if a sharp horizontal blow is delivered against one side of a stacked set of trays.

Oblong openings 102 and 104 are formed in the cover's top panel 36 and are aligned to lie above the handles 42 and 44 on the sides of the tray 12. These openings are dimensioned to permit the handles to extend therethrough in a relatively vertical orientation. Sides 28 and 32 of cover 14 further include vertical slots 106 and 108 that extending from the free edge thereof and terminating in a circular extension whose diameter is greater than the width of its associated slot. The slots 106 and 108 are thus shaped somewhat like a keyhole.

Because some procedures require particular asymmetrical patterns for the arrangement of instruments within the trays, the locks and corresponding slots are not symmetrically located midway along the length of the sides. Instead, the locks and slots are positioned approximately one centimeter closer to sides 20 and 30 than sides 24 and 34, for the purpose of only permitting the cover to be secured to the top of the tray in one position so that the support members affixed to the underside of the cover will be properly in vertical registration with those affixed to the floor of the tray.

The trays, covers and handles are comprised of metal, preferably aluminum, or any rigid material capable of withstanding the elevated temperatures required for steam autoclaving. The locks and feet are also preferably formed of a thermoplastic material, such as Delrin, capable of withstanding high temperatures. The depth of the trays and covers, as well as length and width, are optional and tailored to the requirements of the intended procedure.

Referring again to FIG. 1, a plurality of support members, for holding various medical instruments are affixed to the floor panel 26. Only one such support member is illustrated and is referred to by numeral 110. Additional support members, only one of which (112) is shown in FIG. 1, are adapted to be removably affixed to the underside of the cover panel 36. Because of the uniform distribution of the perforations along the bottom panel 26, the support members may be placed as needed along the surface of the tray to accommodate a wide variety of instrument types. Preferably, they are comprised of resilient, medical grade synthetic rubber or any other soft, resilient, synthetic material capable of tolerating the temperatures and/or chemical sterilants involved.

FIG. 1 shows a complimentary pair of support members 110 and 112, useable with the tray and cover of the present invention. That is, when the cover is installed on the tray, support members 110 and 112 will cooperate with one another to essentially surround an instrument sandwiched therebetween. This permits the entire tray and cover assembly to be turned upside down without allowing release of the instruments. Specially dimensioned, contoured receptacles, as indicated at 114 and 116 are molded or otherwise formed in dimensions appropriate to receive specific instruments. The size and shape of the receptacles are determined by the instruments to be held, but supports without receptacles are also useful when placed in the cover, for holding large instruments within large receptacles in the tray.

The support members 112 and 114 are provided with integrally molded resilient (compressible) feet 118, 120 and 122, 124 which are designed to be pressed through ones of the rectangular openings 40 in the tray's floor 26 and the openings 38 in the cover. Those skilled in the art will appreciate that the rectangular openings are stamped out on a grid pattern which permits the appropriately dimensioned support members to be plugged in at any desired location on the cover or in the tray.

Figure 3:
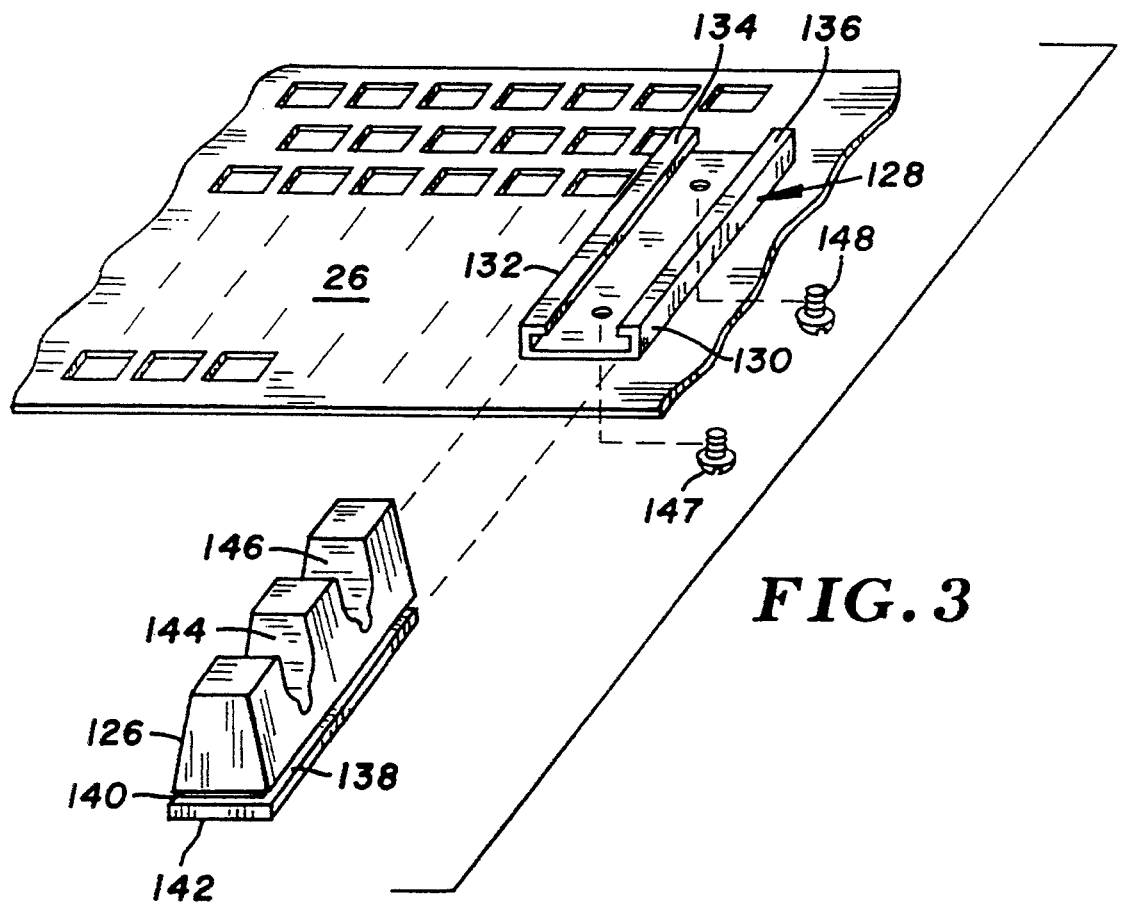
FIG. 3 is a perspective view of a portion of the floor of the tray showing one way of securing the support members thereto.

With reference to FIG. 3, an alternative method of affixing the support members to the tray or cover is shown. It is a perspective view of a section of floor 26. In this arrangement, each support member 126 is inserted into an interchangeable extrusion 128. Each extrusion 128 has sides 130 and 132 which include a pair of inwardly projecting flanges 134 and 136. Grooves 138 and 140 are longitudinally disposed at the base 142 of support member 126 and receive the extrusion's flanges 134 and 136 therein. As in the previously described embodiment, the support member 126 may include a variety of molded sockets 144, 146 which are specially dimensioned to receive specific medical instruments. Screws 147 and 148 are inserted into the plastic or metal extrusions to secure them to the tray or cover.

Figure 4:
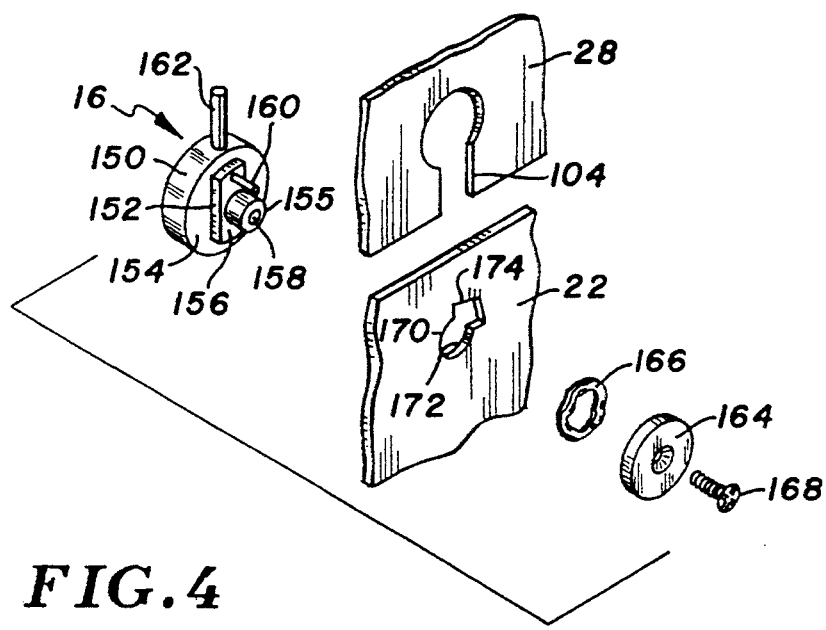
FIG. 4 is a partial, exploded perspective side view of the preferred form for the lock used to secure the cover to the tray.

FIG. 4 shows a partial, exploded view of the locking mechanism employed to securely affix the cover 14 to the tray 12. One lock, indicated generally at 16, is disposed on each of the sides 18 and 22 and, thus, they operate to mechanically engage cover 14 at each end. Each lock includes a molded plastic hub 150, having a generally rectangular, plastic block 152 integrally molded and projecting outward from a planar surface 154 thereof. Projecting outward from the exposed surface 156 of the block 152 is a cylindrical collar 155 having a threaded bore 158 formed centrally therein. A detent pin 160 also projects perpendicularly outward from the surface 156. An actuating pin 162 projects laterally from a side edge of the hub 150, as shown to facilitate rotation of the hub by the user's finger.

The width dimension of the block 152 is more narrow than its height, for reasons that will be described hereinafter.

A plastic retainer 164 and a metal wave washer 166 are disposed on a screw 168, which is inserted through a specially shaped hole 170 stamped through the side 22 and then into the threaded hole 158 in the collar cylindrical 155.

A specially shaped hole 170 is punched or otherwise created in each side which is to receive a lock. The hole 170 has a circular region 172, which is dimensioned to receive the collar 155 of the lock 16 with a close fit. The hole also has a somewhat rectangular section 174 into which detent pin 160 fits. In use, mechanical obstruction between the detent pin and the rectangular segment of the hole confines rotation of the lock to 90°. This provides a visual reference for the user, since the horizontal or vertical orientation of the actuating pin 162 indicates whether the lock 16 is in its open or closed position. It also provides a tactile reference of orientation, depending upon whether it is rotated as far as possible clockwise or counterclockwise.

The outward projection of the block 152 from the surface 154 creates a gap between the exterior of the side 22, and the surface 154 of hub 150. This gap is appropriately dimensioned to permit the thickness dimension of the side 28 of cover 14 to slip therebetween. Sidewall 28 further includes a keyhole channel 108, as previously described, which are dimensioned to allow passage of the block 152 therein when the lock is in its unlocked state. When the lock 16 is rotated by grasping and exerting a force on the actuating pin 162, the block pivots within keyhole channel 108. When pin 162 extends horizontally, the cover is locked to the tray by mechanical obstruction between the block and the keyhole, but when the actuating pin 162 is returned to the vertical, the block becomes aligned parallel to the keyhole channel 108 and is no longer obstructed by it. Now, the tray cover can be removed. The pin 162 for actuating the lock can be readily grasped by a user wearing surgical gloves without snagging or tearing the glove.

Figure 5:
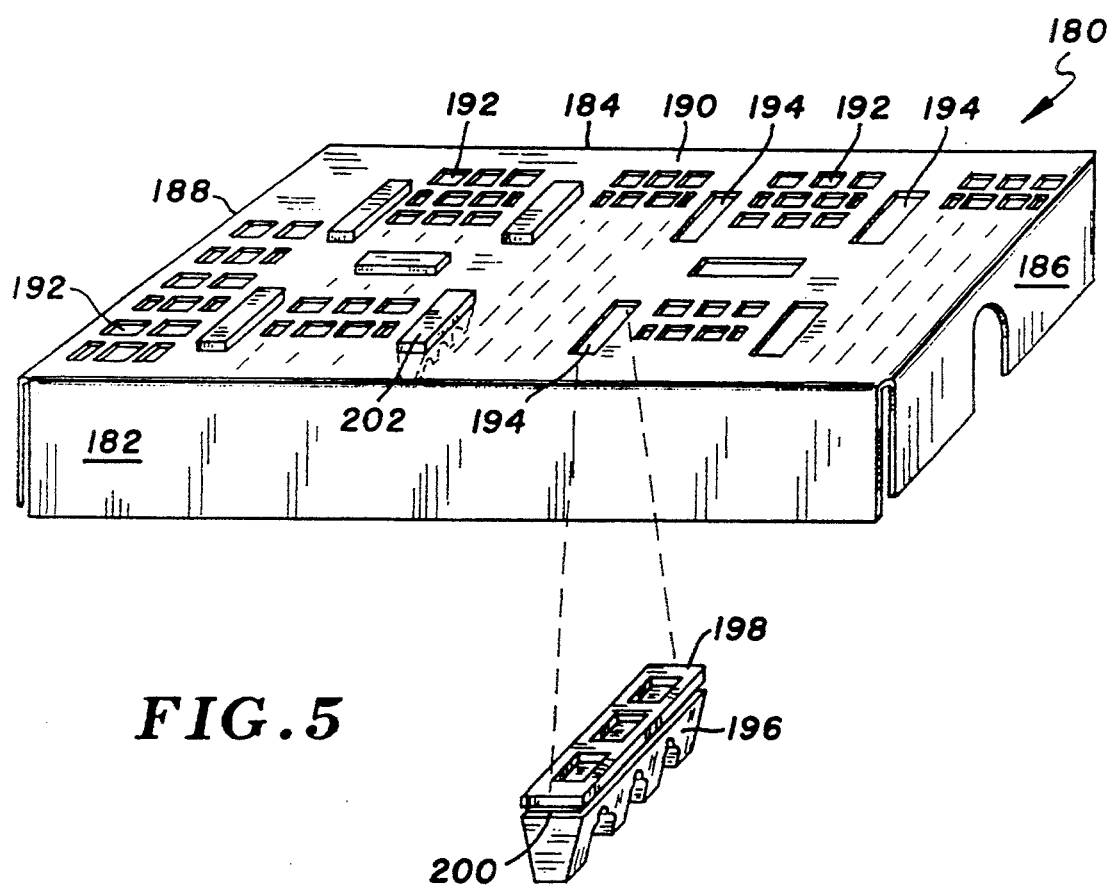
FIG. 5 is a perspective view showing of an alternative way of affixing the support members to an instrument tray assembly.

FIG. 5 is an exploded, perspective view of an alternative tray or cover. It is generally designated by numeral 180 and includes a pair of opposed sides 182 and 184 and opposed ends 186 and 188. The floor or top, as the case may be (190) again has a pattern of perforations as at 192 through which steam or another sterilant may pass. Rather than having these perforations uniformly distributed in a grid pattern over the entire surface of the floor or top 190, in the embodiment of FIG. 5, they are confined to various zones leaving to generally H-shaped patterns which do not contain the small rectangular perforations 192. Instead, a plurality of larger rectangular apertures, as at 194, are formed through the thickness dimension of the floor or top. These larger rectangular openings are designed to accommodate a support member like that identified by numeral 196. The support member 196 differs from those depicted in the embodiment of FIG. 1 and more closely resembles the type identified by numeral 126 in FIG. 3. It includes a resilient, compressible, elastomeric material having a base 198 defined by a peripheral groove 200 extending around the periphery thereof. This permits the support members 196 to be removably plugged into the larger rectangular openings 194 in the fashion identified by reference numeral 202. As can be seen, the edge defining the larger rectangular openings 194 are designed to fit into the peripheral groove 200 when the base 198 is compressed and forced through the associated opening. It can be seen that this arrangement obviates the need for separate extruded channels such as 128 in FIG. 3.

In use, and with reference to FIG. 1, a plurality of instrument support members are selected then positioned along the bottom panel or floor 26 of tray 12. Various medical instruments may then be inserted within the contoured receptacles. Then, a plurality of loaded trays may be stacked upon one another. Alternatively, covers having additional support members may be affixed and several trays stacked with their covers in place.

Depending upon the sterilization procedure to be used, a stack of trays may be wrapped in drapes or inserted directly into a sterilization container, or individual trays, with or without covers, may be wrapped or otherwise contained, then autoclaved. When a plurality of trays are stacked, the unique design of the feet permits them to interlock with adjacent sides of the tray at their corners. Alternatively, the feet may interlock with the circular apertures formed in the covers. Either arrangement permits the trays to withstand a horizontally directed blow without becoming dislodged and without releasing the instruments protected within, whether or not a cover is used.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A tray for use in sterilizing, storing and handling sets of surgical instruments, the tray being stackable on top of a similar tray when the similar tray is uncovered and when the similar tray is covered by a cover having a plurality of apertures, the tray comprising:
   a tray body having a tray floor with an inner surface and an outer surface, and a plurality of tray walls including a pair of opposed tray sides and a pair of opposed tray ends, each of the tray walls is connected to the tray floor and each of the tray sides is connected to each of the adjacent tray ends so as to define a corner therebetween;
   at least one surgical instrument support member removably attached to the inner surface of the tray floor; and
   a plurality of foot members where each foot member is attached to the outer surface of the tray floor, each foot member having a first segment connected to the outer surface of the tray floor, a second segment connected to the first segment and of smaller size than the first segment, and a third segment connected to the second segment and of smaller size than the first segment;
   wherein the first and second segments as the tray define a first shoulder which selectively engages an edge of the tray walls at one of the corners of a similar uncovered tray with the second segment of the tray positioned within the tray walls of the similar uncovered tray and the first segment of the tray resting on the edge of the tray walls of the similar uncovered tray, and the second and third segments of the tray define a second shoulder which selectively engages an area on a of a cover similar covered tray adjacent to an aperture in the cover on the similar covered tray with the third segment of the tray positioned within the aperture of the cover on the similar covered tray and the second segment of the tray resting on the adjacent area around the aperture.

2. The apparatus in claim 1 wherein the tray floor has a plurality of perforations for sterilization means to flow through.

3. The apparatus in claim 1 further comprising a removable cover having a cover top with an inner surface and an outer surface, and a plurality of cover walls including a pair of opposed cover sides and a pair of opposed cover ends, each of the cover walls connected to the cover top and each of the cover sides connected to each of the adjacent cover ends, the pair of opposed cover sides being further apart than the pair of opposed tray sides and the pair of opposed cover ends being further apart than the pair of opposed tray ends to allow cover walls to fit over the tray walls and allow the inner surface of the removable cover to rest on the edge of the tray walls.

4. The apparatus in claim 3 further including at least one surgical instrument support member removably attached to the inner surface of the cover top.

5. The apparatus in claim 4 wherein the tray floor has a plurality of perforations for sterilization means to flow through and the cover top has a plurality of perforations for the sterilization means to flow through.

6. The apparatus as in claim 5 and further including: a handle connected to an inside surface of each of the tray ends and substantially confined to movement within a vertical peripheral boundary set up by the tray walls.

7. The apparatus as in claim 6 wherein the handle is selectively movable in a planar direction between a first position perpendicular to the tray floor and below the edge of the tray ends and a second position perpendicular to the tray floor and raised above the edge of the tray ends, where from the second position the handle are selectively rotatable to a third position parallel to the tray floor.

8. The apparatus as in claim 7 wherein the handle when the inner surface of the removable cover rests on the edge of the tray walls remains within a cavity defined by the tray body and cover thereon when in the first position, while extending outside of the cavity when in the second position.

9. The apparatus as in claim 3 and further including: a locking mechanism for locking the removable cover to at least one of either the tray sides or the tray ends of the tray.

10. The apparatus as in claim 9 wherein the locking mechanism comprises:
first and second knob members rotatably mounted to the opposed tray ends of the tray body, the knob members each including an oblong block of a predetermined length and width dimension;
a keyhole-shaped slot formed in each of the tray ends of the cover, the keyhole-shaped slots having a width dimension greater than the predetermined width dimension of the oblong block, but less than the predetermined length dimension of the oblong block; and
means for rotating the knob member between a first position where the predetermined length dimension of the oblong block is parallel to the keyhole-shaped slot and a second position where the predetermined length dimension of the oblong block is transverse to the keyhole-shaped slot.

11. The apparatus as in claim 10 wherein each of the knob members in the tray body and each of the keyholed shaped slots in the cover are offset closer to one tray side than the other tray side in each of the cover ends and the tray ends respectively.

12. The apparatus in claim 4 further including a tray floor holder for the at least one surgical instrument support member in the tray floor comprising a channel for receiving and retaining the at least one surgical instrument support member therein, the tray floor holder is fastened to the inner surface of the tray floor, and a cover top holder for the at least one surgical instrument support member in the cover top comprising a channel for receiving and retaining one of the surgical instrument support members therein, the cover top holder is fastened to the inner surface of the cover top.

13. The apparatus in claim 12 wherein each surgical instrument support member has a pair of longitudinal grooves which correspond to a pair of inwardly extending flanges, on each channel thereby allowing the surgical instrument support member to be removably slid into the channel.

14. The apparatus in claim 13 wherein each surgical instrument support member has a plurality of molded sockets for receiving and holding surgical instruments.

15. The apparatus as in claim 1 wherein the first segment, the second segment, and the third segment on each foot member are concentric disks, the first segment on each foot member being attached to the outer surface of the tray floor.

* * * * *

UNITED STATES PATENT AND TRADEMARK OFFICE
CERTIFICATE OF CORRECTION

PATENT NO. : 5,384,103
DATED : January 24, 1995
INVENTOR(S) : CURTIS H. MILLER

It is certified that error appears in the above-indentified patent and that said Letters Patent is hereby corrected as shown below:

Col. 1, lines 27-28, delete "occurs", insert --occur--

Col. 5, line 31, delete "feet", insert --foot members--

Col. 5, line 43, delete "extending", insert --extend--

Col. 7, lines 7-8, delete "collar cylindrical", insert --cylindrical collar--

Col. 8, line 62, delete "as", insert --of--

Col. 9, line 3, delete "of a"

Col. 9, line 3, after "cover", insert --of a--

Col. 9, line 45, delete "are", insert --is--

Col. 10, line 36, delete "one of the", insert --the at least one--

Col. 10, line 37, delete "members", insert --member--

Col. 10, line 42, after "flanges", delete the ","

Signed and Sealed this

Ninth Day of May, 1995

*Attest:*

BRUCE LEHMAN

*Attesting Officer*   Commissioner of Patents and Trademarks